United States Patent
Barnes et al.

(10) Patent No.: US 8,435,183 B2
(45) Date of Patent: *May 7, 2013

(54) BALANCE BODY ULTRASOUND SYSTEM

(75) Inventors: Stephanie A. Barnes, Bothell, WA (US); Steven M Bunce, Sedro Woolley, WA (US); Bryan S. Cabatic, Seattle, WA (US); Blake W. Little, Bothell, WA (US); Bill Purdue, Mill Creek, WA (US); John D. Schultz, Bothell, WA (US); Kari L. Rice, Bothell, WA (US)

(73) Assignee: SonoSite, Inc., Bothell, WA (US)

( * ) Notice: Subject to any disclaimer, the term of this patent is extended or adjusted under 35 U.S.C. 154(b) by 2427 days.

This patent is subject to a terminal disclaimer.

(21) Appl. No.: 10/404,220

(22) Filed: Mar. 31, 2003

(65) Prior Publication Data
US 2003/0195418 A1    Oct. 16, 2003

Related U.S. Application Data

(60) Division of application No. 10/227,160, filed on Aug. 21, 2002, now Pat. No. 6,575,908, which is a continuation-in-part of application No. 10/009,474, filed on Mar. 15, 2002, now Pat. No. 7,819,807.

(51) Int. Cl.
*A61B 8/14*    (2006.01)
(52) U.S. Cl.
USPC ............ 600/459; 600/437; 600/443; 600/446
(58) Field of Classification Search .................. 600/437, 600/443, 446, 459
See application file for complete search history.

(56) References Cited

U.S. PATENT DOCUMENTS

| | | | |
|---|---|---|---|
| 3,964,296 A | 6/1976 | Matzuk | |
| 5,293,351 A | 3/1994 | Noponen | |
| 5,295,485 A * | 3/1994 | Shinomura et al. | 600/443 |
| 5,394,875 A | 3/1995 | Lewis et al. | |
| 5,555,534 A | 9/1996 | Maslak et al. | |
| 5,590,658 A | 1/1997 | Chiang et al. | |
| 5,617,864 A | 4/1997 | Stouffer et al. | |
| 5,647,366 A | 7/1997 | Weng | |

(Continued)

FOREIGN PATENT DOCUMENTS

| DE | 2003/10224234 | 1/2003 |
|---|---|---|
| EP | 713 102 | 5/1996 |

(Continued)

OTHER PUBLICATIONS

Armitage et al.,(1995). "An integrated array transducer receiver for ultrasound imaging," *Sensors and Actuators*, A 46-47:542-546.

(Continued)

*Primary Examiner* — Long V. Le
*Assistant Examiner* — Ellsworth Weatherby

(57) ABSTRACT

The present invention relates to a hand held ultrasound system having a balance body, a transducer assembly connected to said balance body via a communication means and a plurality of control elements arranged in an ergonomic fashion on said balance body, such that a user may hold said system and operate at least one of said control elements with the same hand. In particular a medical ultrasound system comprising a balance body incorporating system electronics, a power supply and a user interface wherein the user interface comprises a D-controller and a touch screen and a transducer assembly attached to the balanced body by a cable.

5 Claims, 24 Drawing Sheets

U.S. PATENT DOCUMENTS

| | | | |
|---|---|---|---|
| 5,655,535 | A | 8/1997 | Friemel et al. |
| 5,709,209 | A | 1/1998 | Friemel et al. |
| 5,722,412 | A | 3/1998 | Pflugrath et al. |
| 5,795,297 | A | 8/1998 | Daigle |
| 5,817,024 | A | 10/1998 | Ogle et al. |
| 5,826,042 | A * | 10/1998 | Kirkendoll ............ 710/303 |
| 5,839,442 | A | 11/1998 | Chiang et al. |
| 5,860,924 | A | 1/1999 | Quistgaard |
| 5,893,363 | A | 4/1999 | Little et al. |
| 5,935,074 | A | 8/1999 | Mo et al. |
| 6,048,319 | A | 4/2000 | Hudgins et al. |
| 6,054,922 | A * | 4/2000 | Smith ................. 340/568.1 |
| 6,126,608 | A | 10/2000 | Kemme et al. |
| 6,135,961 | A | 10/2000 | Pflugrath et al. |
| 6,248,073 | B1 | 6/2001 | Gilbert et al. |
| 6,251,073 | B1 | 6/2001 | Imran et al. |
| D462,446 | S | 9/2002 | Felix et al. |
| 6,447,451 | B1 * | 9/2002 | Wing et al. ............ 600/437 |
| D467,002 | S | 12/2002 | Felix et al. |
| D469,539 | S | 1/2003 | Felix et al. |
| D469,877 | S | 2/2003 | Felix et al. |
| 6,530,887 | B1 * | 3/2003 | Gilbert et al. ......... 600/459 |
| 6,532,152 | B1 * | 3/2003 | White et al. .......... 361/692 |
| 6,561,979 | B1 | 5/2003 | Wood et al. |
| 6,569,101 | B2 | 5/2003 | Quistgaard et al. |
| 6,569,102 | B2 | 5/2003 | McLaughlin et al. |
| 6,575,908 | B2 * | 6/2003 | Barnes et al. ......... 600/443 |
| 6,618,206 | B2 | 9/2003 | Tarakci et al. |
| 6,663,567 | B2 | 12/2003 | Ji et al. |
| 6,685,645 | B1 | 2/2004 | McLaughlin et al. |
| 6,733,455 | B2 | 5/2004 | Mo et al. |
| 6,773,399 | B2 | 8/2004 | Xi et al. |
| 6,866,631 | B2 | 3/2005 | McLaughlin et al. |
| 6,866,632 | B1 | 3/2005 | Chou et al. |
| 6,896,658 | B2 | 5/2005 | Ji et al. |
| 6,936,008 | B2 | 8/2005 | Tarakci et al. |
| 6,962,566 | B2 | 11/2005 | Quistgaard et al. |
| 6,980,419 | B2 | 12/2005 | Smith et al. |
| 7,022,075 | B2 | 4/2006 | Grunwald et al. |
| 7,115,093 | B2 * | 10/2006 | Halmann et al. ............ 600/437 |
| 2002/0173721 | A1 | 11/2002 | Grunwald et al. |
| 2003/0004414 | A1 | 1/2003 | McLaughlin et al. |
| 2003/0009102 | A1 | 1/2003 | Quistgaard et al. |
| 2003/0013959 | A1 | 1/2003 | Grunwald et al. |
| 2003/0013965 | A1 | 1/2003 | Quistgaard et al. |
| 2004/0138569 | A1 | 7/2004 | Grunwald et al. |
| 2005/0131294 | A1 | 6/2005 | Ji et al. |
| 2006/0025684 | A1 | 2/2006 | Quistgaard et al. |
| 2006/0116578 | A1 | 6/2006 | Grunwald et al. |

FOREIGN PATENT DOCUMENTS

| | | |
|---|---|---|
| EP | 763 344 | 3/1997 |
| EP | 815 793 | 1/1998 |
| WO | WO 94/23421 | 10/1994 |
| WO | WO 01/13796 | 3/2001 |
| WO | WO 2004/080364 | 9/2004 |

OTHER PUBLICATIONS

Hatfield et al., (1995). "High Frequency Ultrasonic Scanning System," *38th Midwest Symposium on Circuits and Systems*: Rio De Janeiro, Aug. 13-16, 1995; pp. 1175-1178.

Kim et al., (1987). "Pipelined Sampled-Delay Focusing in Ultrasound Imaging Systems," *Ultrasonic Imaging*, 9:75-91.

* cited by examiner

BALANCE BODY ULTRASOUND SYSTEM

CROSS-REFERENCES TO RELATED APPLICATIONS

The present application is a divisional of U.S. Ser. No. 10/227,160, now U.S. Pat. No. 6,575,908, which was a continuation-in-part of U.S. Ser. No. 10/099,474, filed on Mar. 15, 2002, now U.S. Pat. No. 7,819,807, the full disclosures of which are incorporated herein by reference.

BACKGROUND OF THE INVENTION

1. Field of the Invention

This invention relates to handheld ultrasound instruments having various diagnostic modes and transducer assemblies incorporating a balance body design, or other form factor to reduce strain of use during scanning procedures.

2. Description of the Background Art

As is well known, modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of digital electronics, it is now possible to foresee a time when ultrasound systems will be able to be miniaturized to a size even smaller than their much earlier ancestors. The physician is accustomed to working with a hand held ultrasonic scanhead that is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

tendency has been the smaller systems also lose attributes of their larger stationary cousins due to limitations in space and power availability, the same factors that increase portability. An inverse relation exists between size and feature set. The use of digital beamformers and digital signal processing has allowed the expansion of capabilities of the smaller, more portable ultrasound systems relative to their predecessors. Recent releases of product like the SonoSite 180 have demonstrated the ability of manufacturers to reduce the size and weight of an ultrasound system while still delivering acceptable performance. As technology improves in both digital signal processing and power management, there remains a need for providing a hand held or portable ultrasound system that delivers acceptable performance characteristics, and at the same time is easy to use. There also remains a need for providing a method of being able to reduce costs to the users of ultrasound systems by providing an affordable and easily obtainable upgrade path to such user friendly ultrasound systems, both for hardware elements, and software.

BRIEF SUMMARY OF THE INVENTION

The present invention relates to hand held ultrasound systems providing the advances of digital signal processing and advanced human factors usability. The various design elements of the ultrasound systems presented herein are based on a series of common system electronics detailed in previously listed co-pending applications.

The present invention is a diagnostic hand held ultrasound system weighing less than three and a half pounds (3.50 lbs), including a battery, display screen and system electronics within a common enclosure and a transducer. The common enclosure comprises a balance body design having an aperture, said aperture having a design for operating as a handle. A plurality of control elements are positioned substantially near the aperture such that a person may carry said system and utilize at least one of the plurality of control elements with the a single hand. Also a main board having the battery and the system electronics arranged such that the aperture is positioned at least partially between the battery and the system electronics. A sample data beamformer and at least one digital signal processor (DSP) capable of producing 2D and 3D images are contained within the system electronics.

In a second embodiment of the present invention, a medical ultrasound system comprising a balance body incorporating system electronics, a power supply and a user interface wherein said user interface comprises a D-controller and a touch screen and a transducer assembly attached to said balanced body via a cable. Control of the control of the medical ultrasound device is achieved through selecting through a series of window menus either by using the D-controller or the touch screen or a combination of both. The second embodiment is lightweight and preferably weighs less than three and a half (3.50 lbs) pounds and the balance body can be held with the same hand that operates the D-controller. Optionally the system further comprises an I/O port for connecting to a docking station, and a handle.

In a third embodiment, we describe a lightweight diagnostic ultrasound instrument comprising a body having a power supply, a user interface for controlling the instrument, a display screen, and a system electronics package capable of a plurality of diagnostic ultrasound modes, said body weighing less than three pounds; a transducer assembly comprising a digital beam former, an A/D converter circuit, and a transducer array, the transducer assembly weighing less than one pound; and a wire connecting said body and said transducer assembly, the wire having a path for feeding power from the power supply to the transducer assembly, and a signal path for transmitting digital signals between the system electronics and the transducer assembly.

In a fourth embodiment we describe a wireless diagnostic ultrasound system comprising; a first body having system electronics, a user interface having a display screen and at least one control element, a first wireless transmit/receive element and a first power supply, said first body weighing less than two pounds; and a second body having a digital beam former, an A/D converter circuit, a transducer array, a second power supply, and a second transmit/receive element such that the digital beam former can be controlled by the system electronics via the first and second transmit/receive elements, said second body weighing less than one pound.

In still another embodiment, we describe a lightweight medical ultrasound system comprising a first body having system electronics, a first transmit/receive element and a first power supply, said first body weighing less than two pounds; a second body having a digital beam former, an A/D converter circuit, a transducer array, a second power supply, a second transmit/receive element and at least one control element, said second body weighing less than one pound; and a headset comprising a visual display, a receive element and a third power supply such that the first body, second body and head set are in communication with each other through the first and second transmit/receive element and the receive element so that a user may control the system through the at least one control element of the second body, while the first body performs the diagnostic operations through said system electronics, and the user may see the operations through the visual display of the head set.

In yet another embodiment, we describe a system as detailed above wherein the first body and the second body are incorporated into a single transducer assembly weighing less than two pounds and sharing a single power supply and having a single transmit/receive element.

Methods of using the various embodiments are also provided. These and other embodiment of the present invention will become readily apparent upon a detailed inspection of the detailed description of the invention, and a study of the appended claims.

DETAILED DESCRIPTION OF THE INVENTION

Several terms have been clarified here to facilitate an understanding of the present invention.

Balance Body: A design for an ultrasound device wherein the center of gravity for the device is positioned close to the strength of a users hand. By shifting components around in the internal arrangement of the device, an aperture can be made in the device body where system electronics and other essential elements are, such that the device body is balanced for more comfortable holding in a users hand.

D-Controller: Any of a variety of control devices allowing a user to "point and click." The D-controller may be a digital directional controller (such as a four or eight directional controller), an analog "joy stick." The D-Controller allows a user to navigate an on-screen menu or displayed graphics similar to the use of a touch pad or lap top "nipple" pointing style device.

The present invention described a hand held ultrasound system having a balance body, a transducer assembly connected to said balance body via a connection means, and a plurality of control elements arranged in an ergonomic fashion on the balance body. The system is designed such that a user may hold the balance body and operate a key control element, such as a D-controller, with the same hand.

Figure 1A:
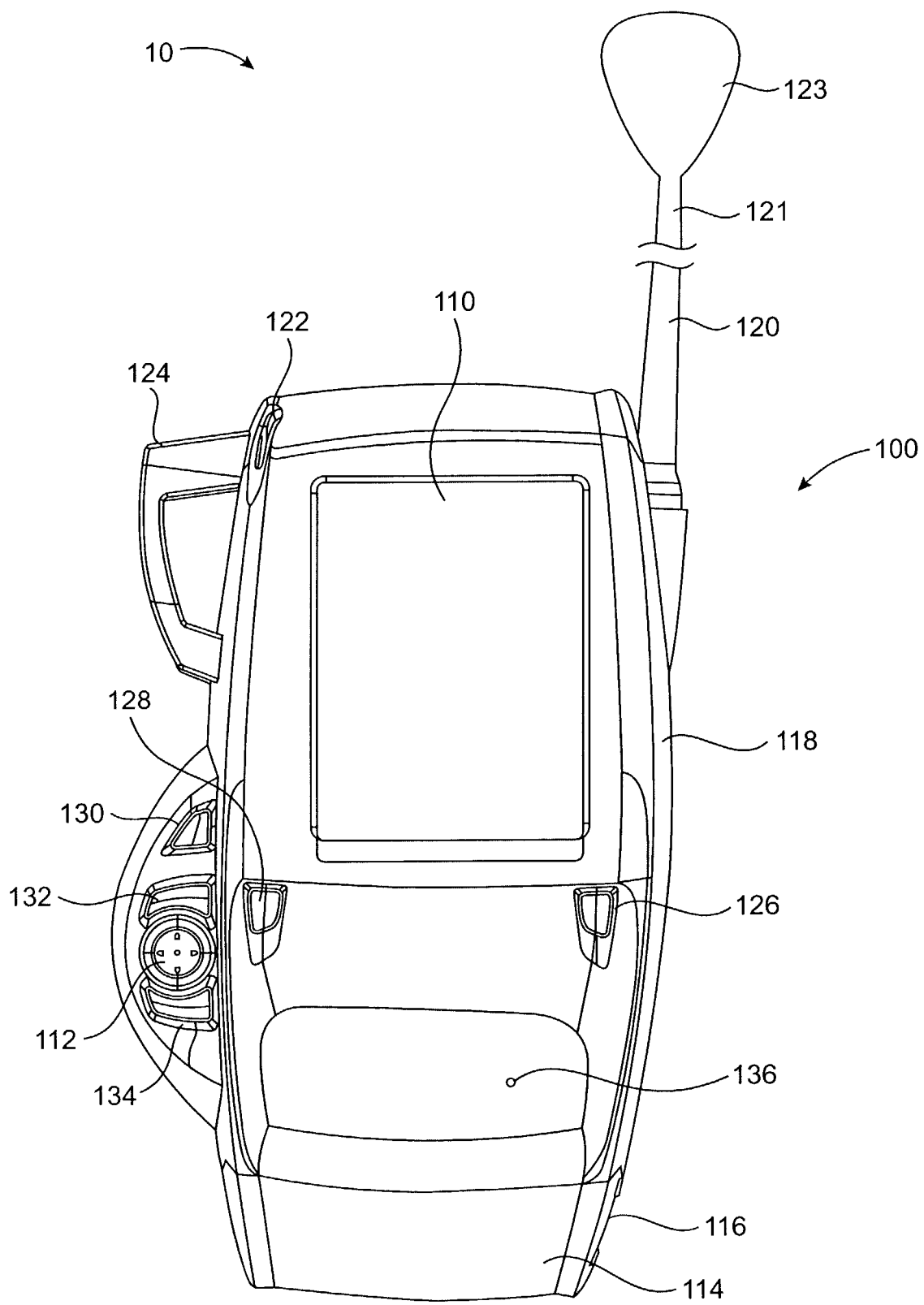
FIG. 1A-D illustrates a balance body ultrasound device of the present invention.
Figure 1B:
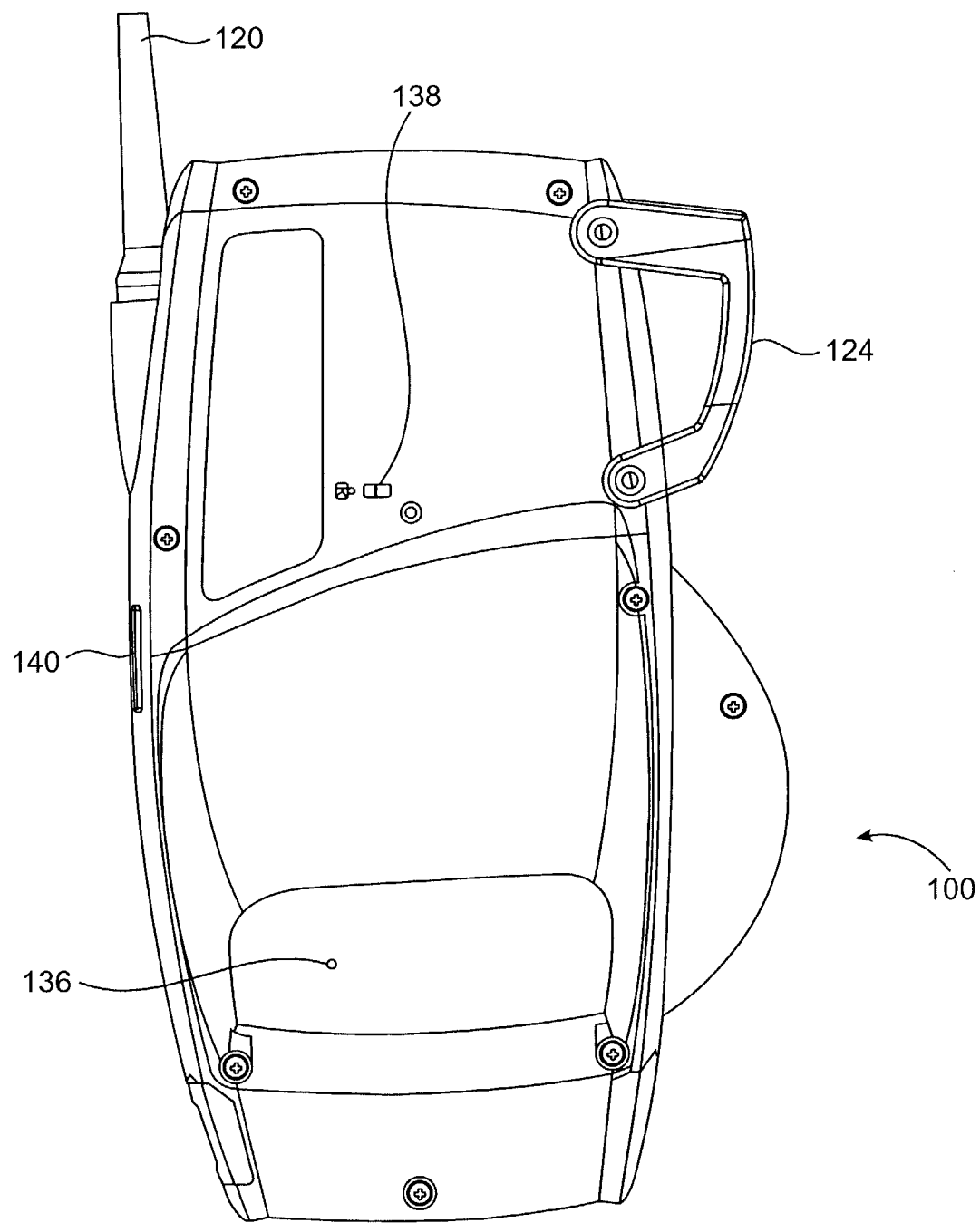
Figure 1C:
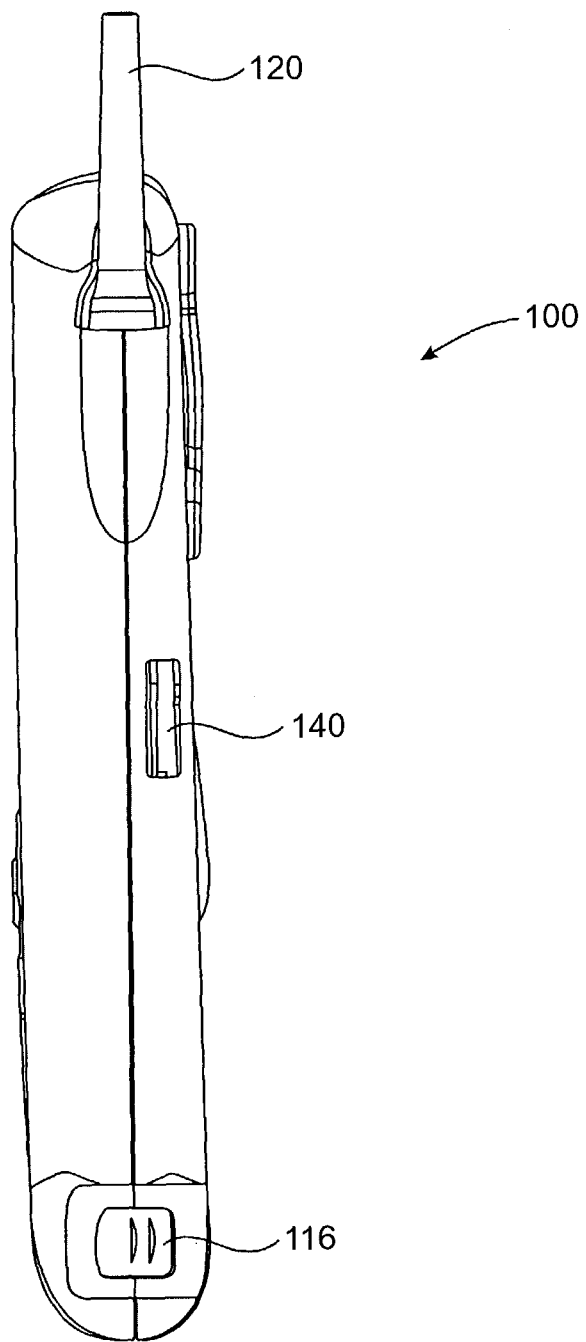

Turning now to FIGS. 1A-1C, a medical ultrasound system 10 comprises a balance body 100 incorporating system electronics, a power supply and a user interface wherein the user interface comprises a D-controller 112 and a touch screen 110, the transducer assembly 123 is connected to the balance body 100 via a cable 121 extending from a cable port 120.

The balance body 100 is a housing containing the system electronics, power supply and user interface. The balance body 100 has an aperture 136 through which a user may insert his or her hand. The aperture 136 is shaped to be comfortable for the majority of users. The balance body 100 has the aperture 136 for the users hand arranged so the users palm and fingers support the weight of the device by being essentially flat against the backside of the balance body 100. The users thumb wraps around to the front face of the balance body 100, and the D-controller 112 is positioned such that the users thumb can easily manipulate the D-controller 112 while the users palm and fingers support the weight of the balance body. In one embodiment, the power supply is located in the handle 114, opposite the system electronics (the aperture for a users hand being between the power supply and the system electronics). Since the power supply is one of the heavier element of the medical ultrasound system 10, the counter balancing effect makes the medical ultrasound system 10 easier to use and hold through the aperture 136. A power supply release button 116 is provided when necessary to remove the power supply within the handle 114.

A plurality of control elements or buttons 128, 132, 134 are also accessible to the users thumb, these control buttons or control elements are arrayed about the D-controller 112 so the user does not have to extend the thumb into an awkward position in order to actuate these control elements. Additional control elements 130, 126, such as the on/off switch 126 are purposefully positioned out of reach of the users thumb, thus avoiding inadvertently turning the system off during a medical scan. The control elements need not be buttons per se. The present invention can also operate using a series of touch pads that would supplement the primary D-controller 112, or utilize spring loaded dials that may be adjusted, then depressed below the surface of the balance body. The screen 110 is preferably a touch screen, and a stylus 122 is incorporated into the balance body 100 so a user may use the stylus 122, fingers (of the users second hand), or the D-controller 112 to input information through the touch screen 110. It should be noted here the D-controller 112 can also be used to position a pointer in a graphics image. In this manner a user may select an area of an image for enhanced viewing, or gain additional information about an icon on the screen or data about a scan image, or perform a manual trace of a scan image. The touch screen 110 has a plurality of image presentation styles, and among them is a QWERTY style keyboard so a user can input information such as patient data, or notes from an ultrasound scan.

The transducer assembly 123, or scan head comprises a transducer array and an inter-connector for coupling the transducer array to the cable. The transducer assembly 123 is connected to the balance body 100 by a cable 121 that feeds control signals to the transducer array (for steering, scan mode, etc.) as well as power from the power supply in the balance body 100. The transducer assembly 123 may be permanently affixed to the balance body through the cable 121, or the cable may be removable such that a different scan head/transducer assembly can be attached to the balance body.

Additional features that may be incorporated onto the balance body include a holster 124 for retaining the transducer assembly 123 when not in use, a receptacle for placement of the stylus, an aperture 138 on the back side for connecting a locking pin into the balance body (when placed into a docking station), a spacer (not shown) for use in the aperture to accommodate smaller user hands and increase the user audience able to use the system and a hinge for the display screen so it can be tilted or swiveled. A data I/O port 140 is provided for communication with a docking station (not shown).

Dimensionally, the medical ultrasound system of the present embodiment has a total system weight under three and one half pounds (3.50 lbs). The cable is of varying length but is designed to be sufficient for a user to comfortably hold the balance body in the users field of view and scan a patient simultaneously. The balance body comprises the bulk of the weight while the transducer assembly generally weighs less than eight ounces (0.5 lbs). The balance body measures less than twelve inches long, seven inches in height and two inches in depth (12"×7"×2") not including the transducer assembly and attaching cable.

Figure 21:
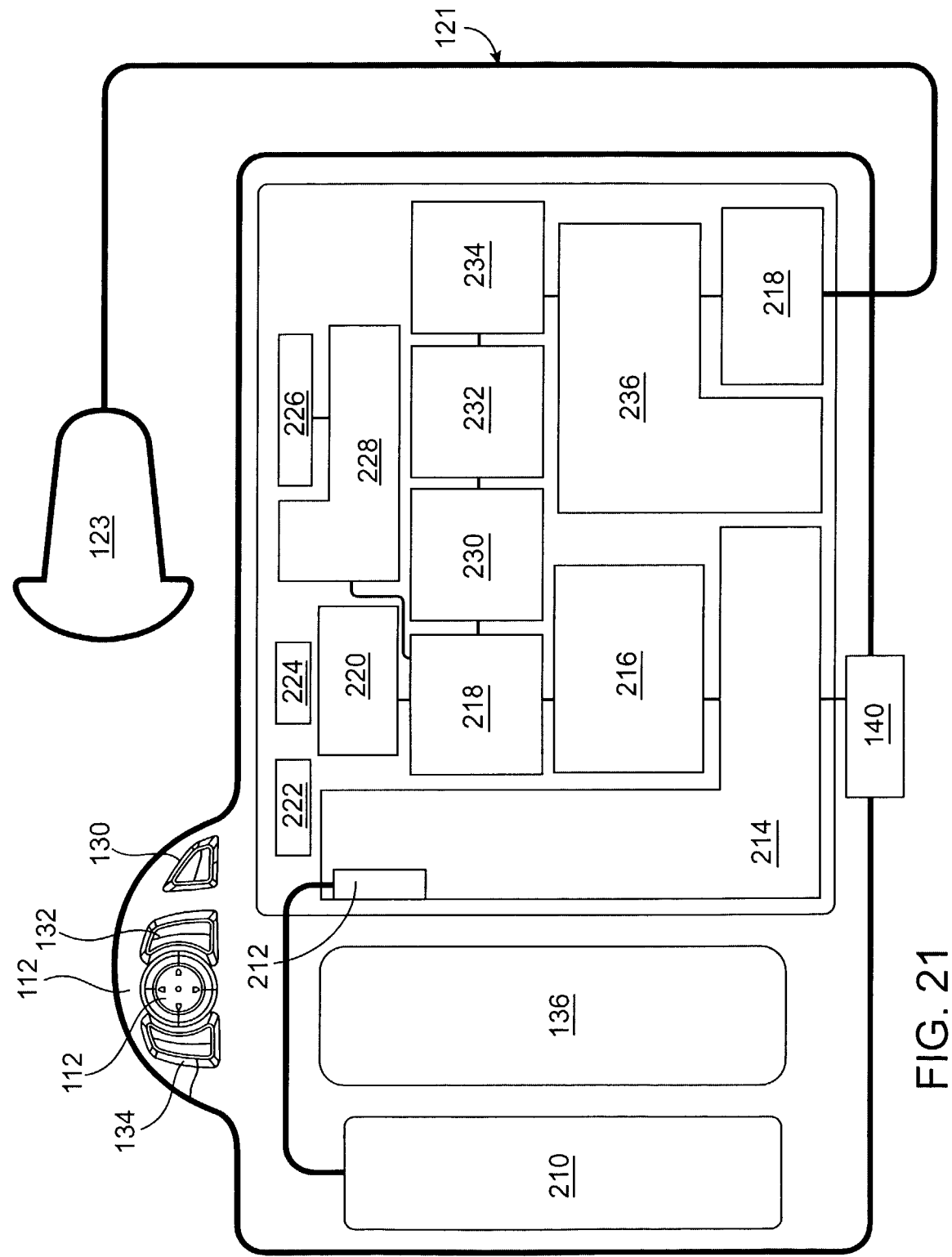
FIG. 21 illustrates a hardware layout useable with the present invention.

FIG. 21 illustrates a hardware map of the main components of the present invention in order to create the balance body design. The power supply 210 is positioned opposite the main board. An aperture 136 for the placement of the users hand is positioned to separate the battery (or battery pack) 210 and main board. Sine the battery 210 is the heaviest component of the entire system, it offsets the weight of the rest of the system electronics, display and body so the center of gravity for the balance body remains close to the aperture 136. Ideally the center of gravity is focused at the strength of the users hand, such as the palm area. The battery pack 210 connects to the battery connector 212 providing energy to the power supply and control 214. Regulation of the power used by the various components of the ultrasound system is critical to maintain the small size and operation of the device. A user interfaces with the unit through a touch screen (and touch screen circuitry 220) and the various user input devices. The commands go to the CPU 218 and the ultrasound machine performs the scans the user desires, and the unit is capable of doing. Memory chips 216 contain program information including what scan modes the unit is capable of performing, and what parameters a user can measure or interact with (such as spatial smoothing or manual adjustment for electronically steering the ultrasound beam). Data from individual scans may also be stored here in the memory chips 216. In an alternative embodiment, the memory chips 216 may be augmented by a persistent memory means in the form of a computer style hard drive, although such a drive must conform to the size and power restrictions inherent in the use of the system.

Operationally, the CPU 218 directs the control circuitry 230 with the desired scan type. A digital signal processor 232, beamformer 234, A/D converter and transmit and receive circuits 236 direct the transducer 123 through a transducer connector 238 to form the desired ultrasound scan mode. The various elements of the transmit and receive path may be consolidated into one or more ASIC chips to further reduce size, and power consumption of the unit.

The user interfaces with the various control elements and touch screen through the BL connection 222 and touch screen connection 224. Information passing through the touch screen goes through the touch screen circuitry 220 to the CPU 218. Display information passes from the CPU 218 to the LCD drive circuitry 228 and to the LCD connector 226.

It is consistent with the teachings of the present invention to separate the beamformer, A/D converter, analog transmit and receive elements into a transducer with a separate battery (not shown) and a wireless transmit/receive antenna for digital signal to the main body containing the system CPU, memory, display and User Interface (UI). The main body having its own battery and transmit/receive antenna to communicate with the fully integrated wireless scan head.

Figure 1D:
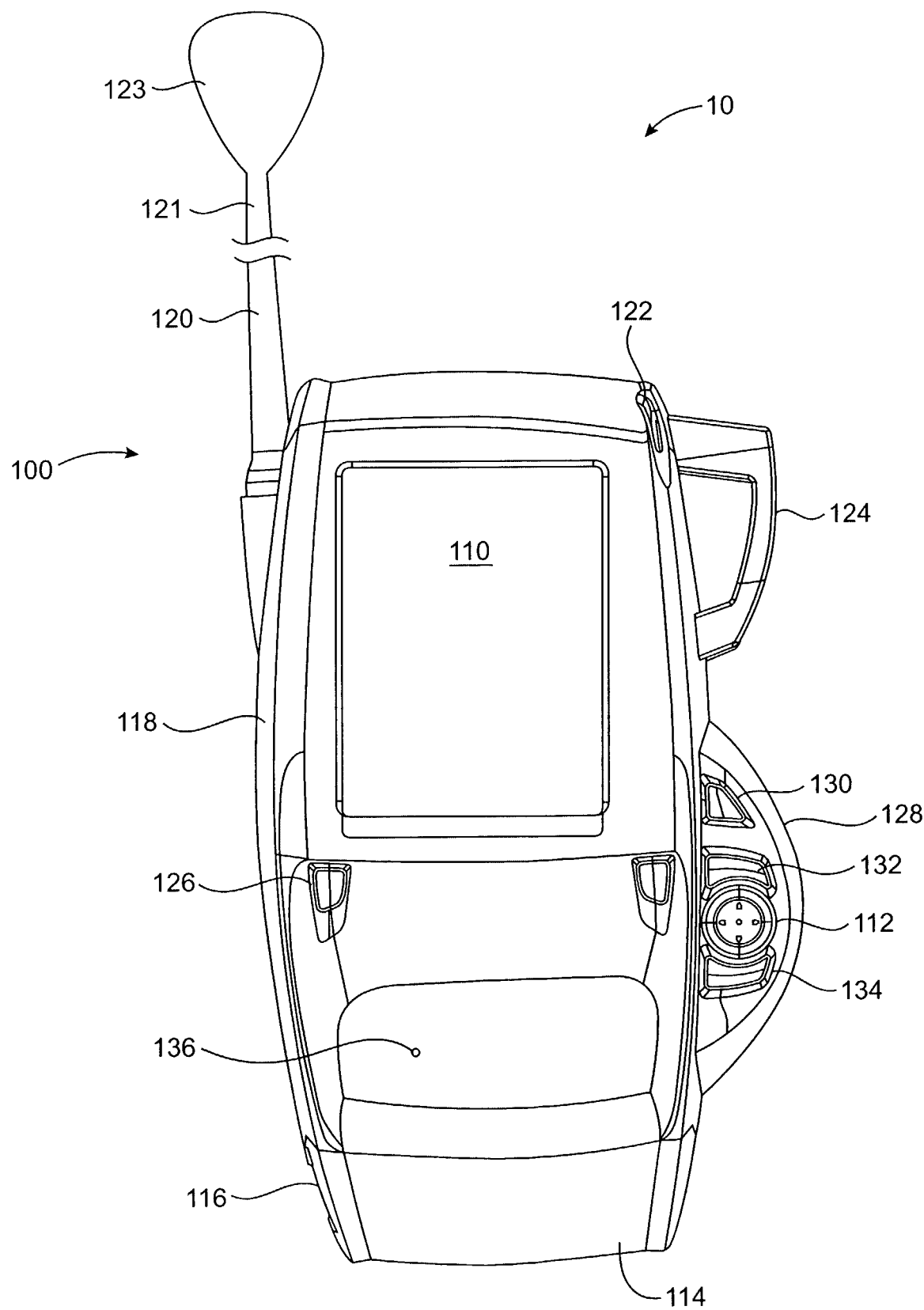
Figure 2:
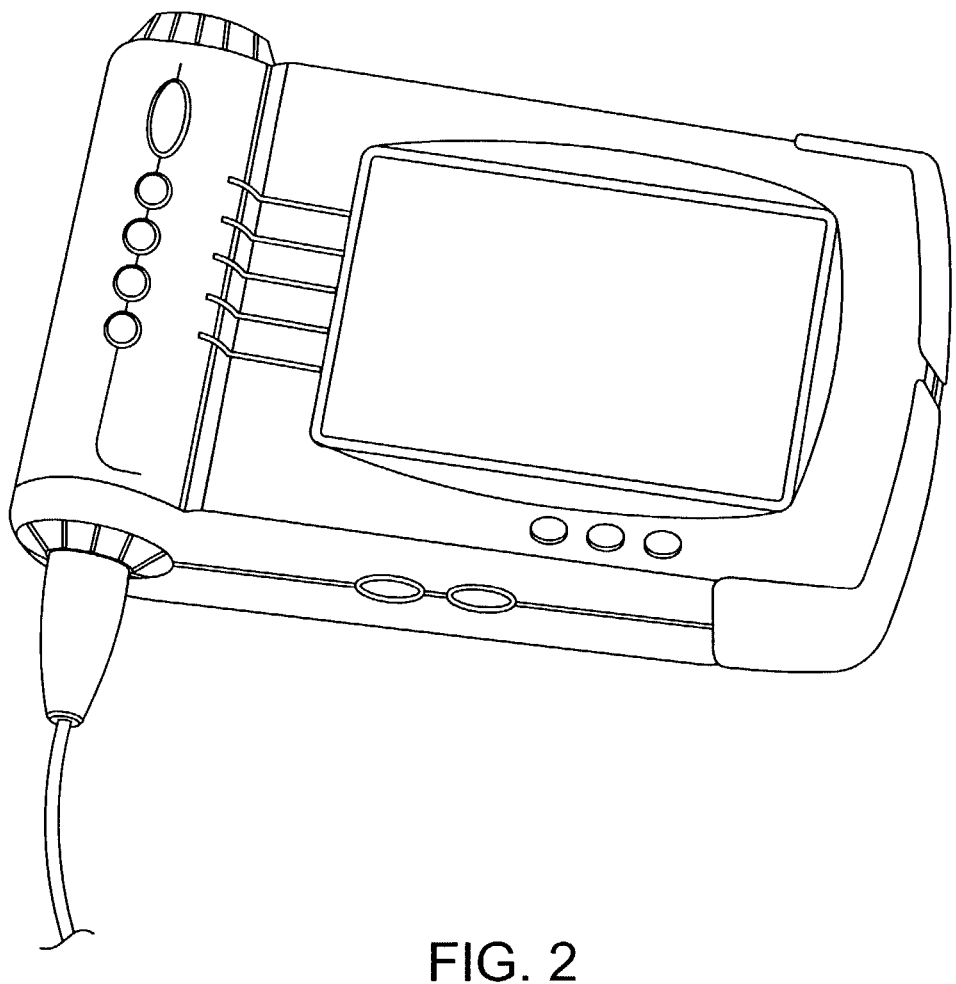
FIGS. 2-20 illustrate alternative embodiments of the present invention.
Figure 3:
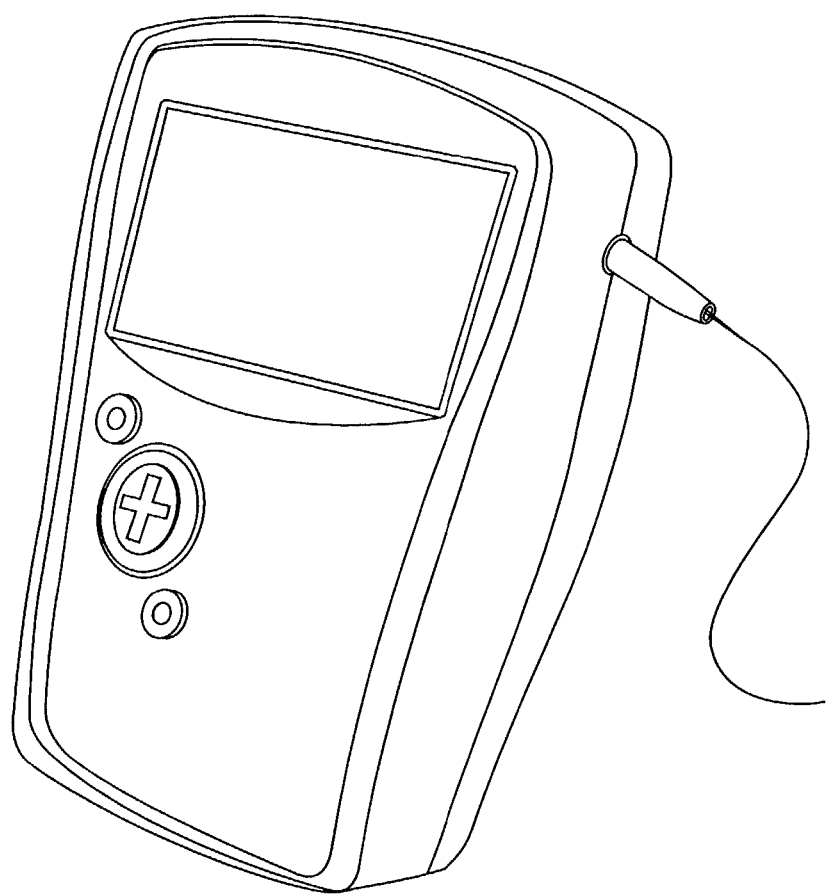
Figure 4:
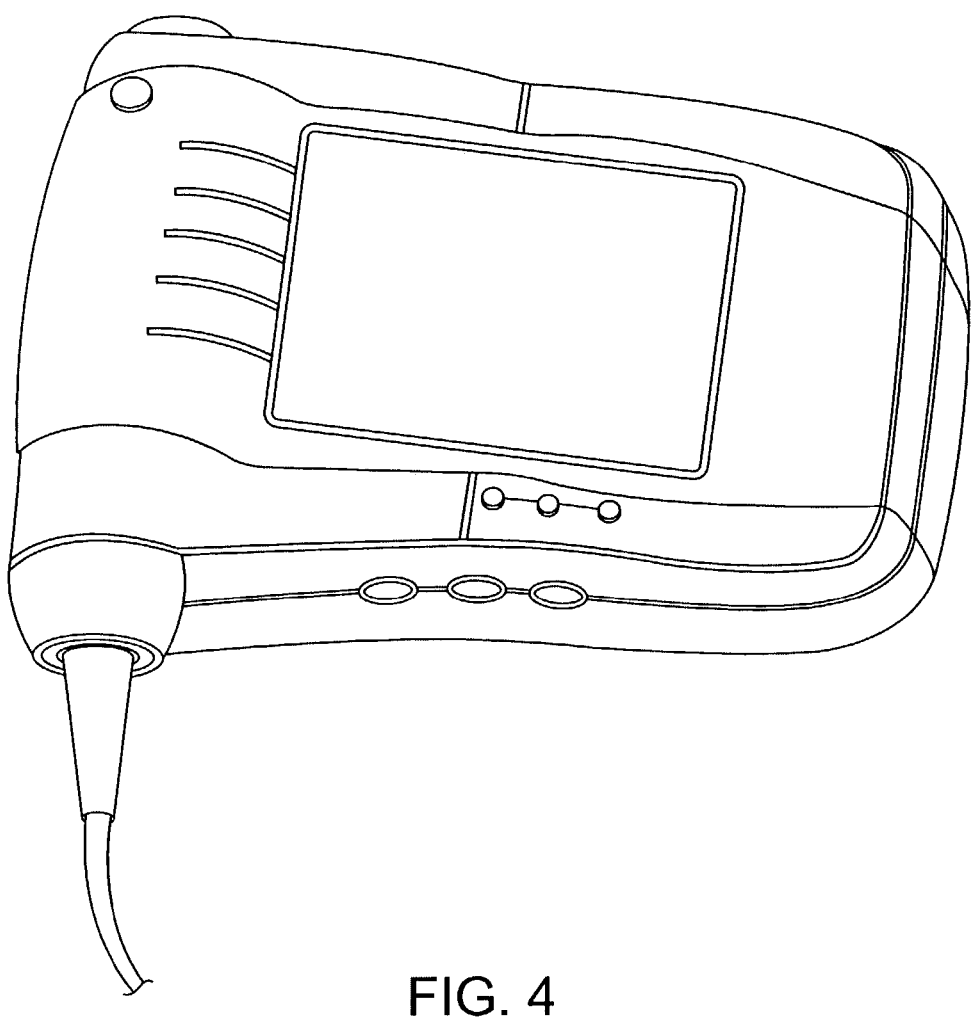
Figure 5:
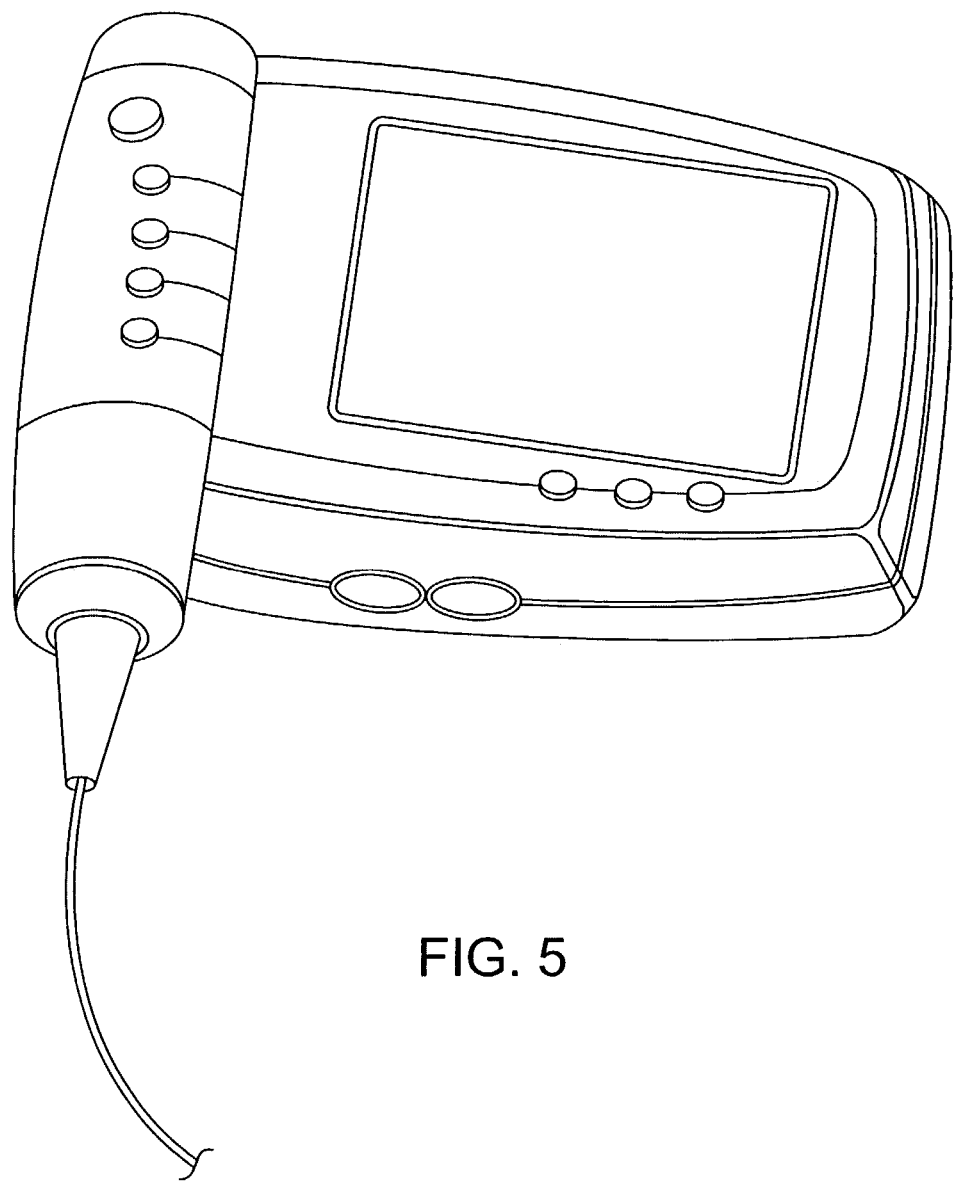
Figure 6:
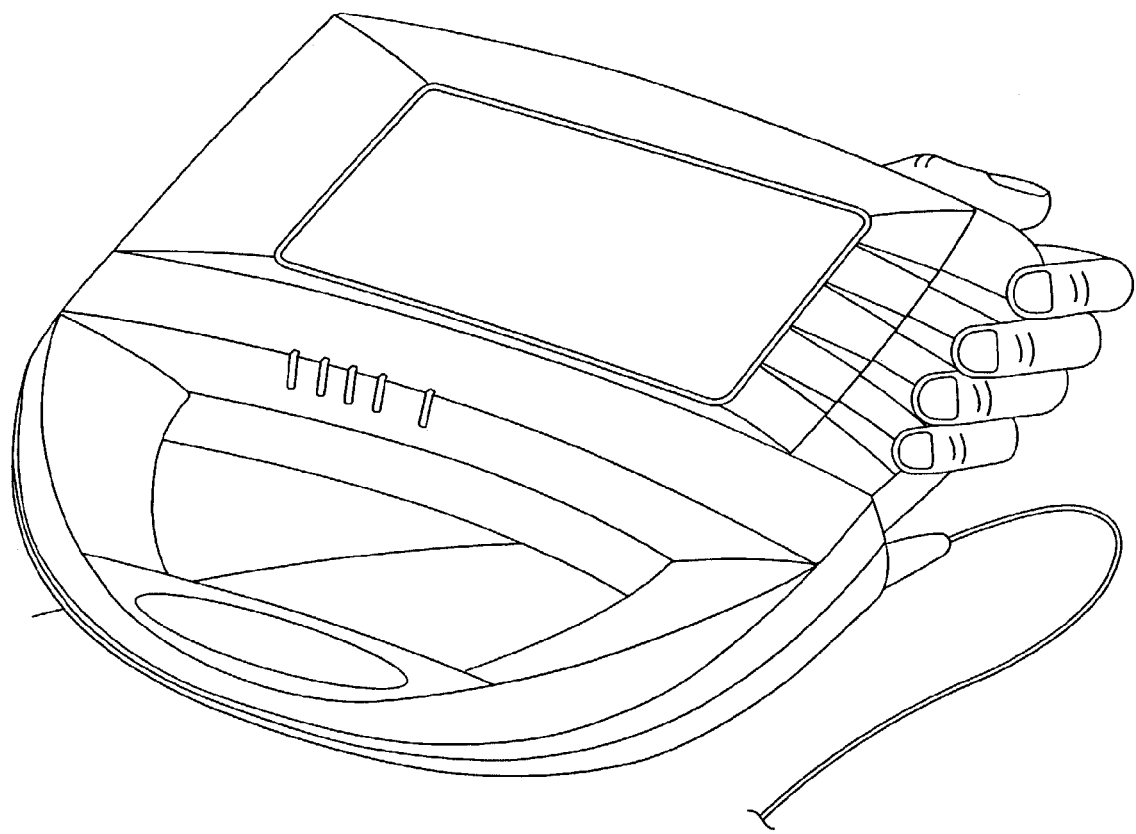
Figure 7B:
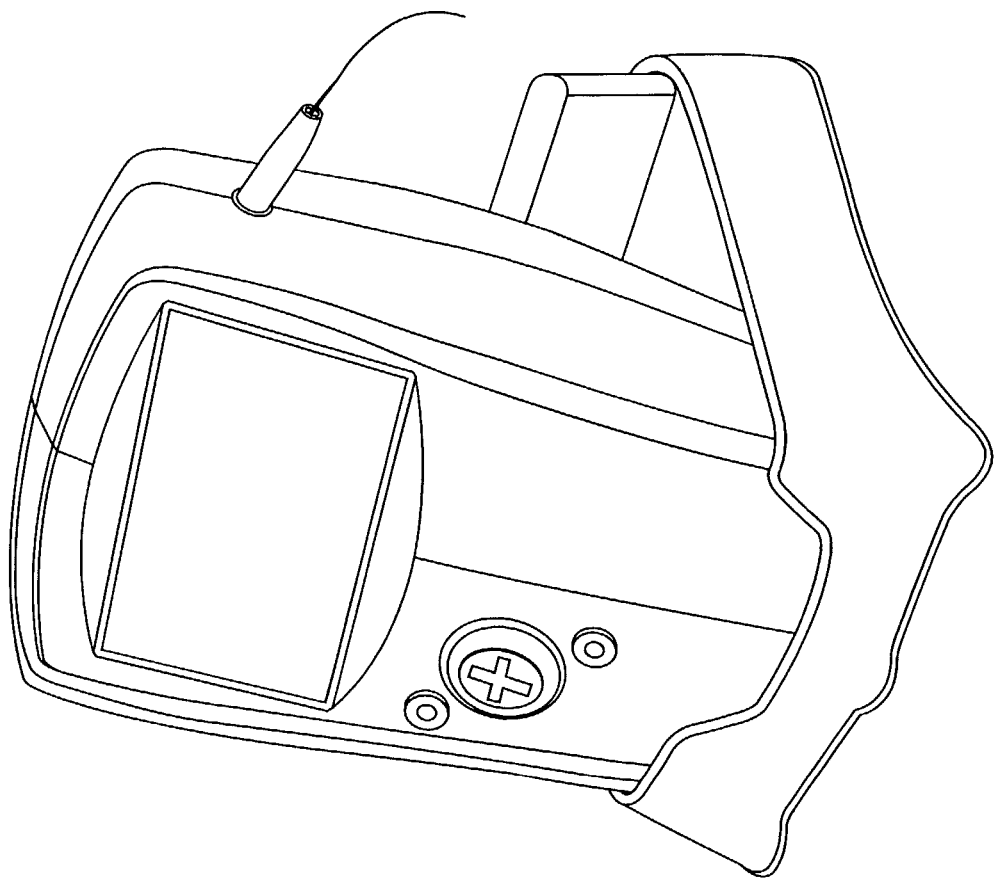
Figure 7A:
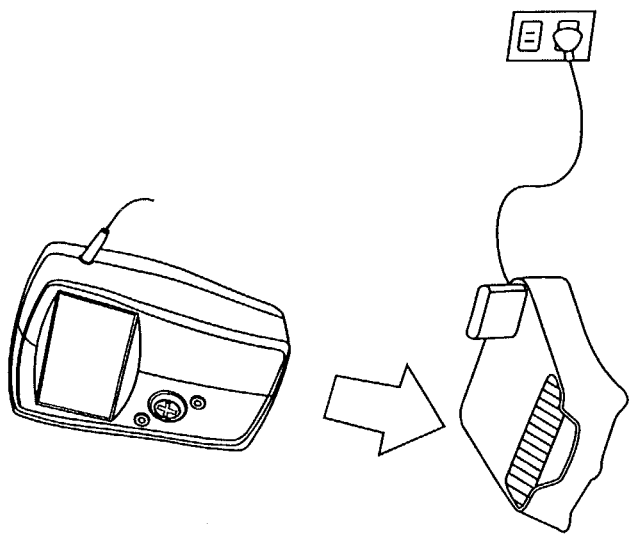
Figure 8:
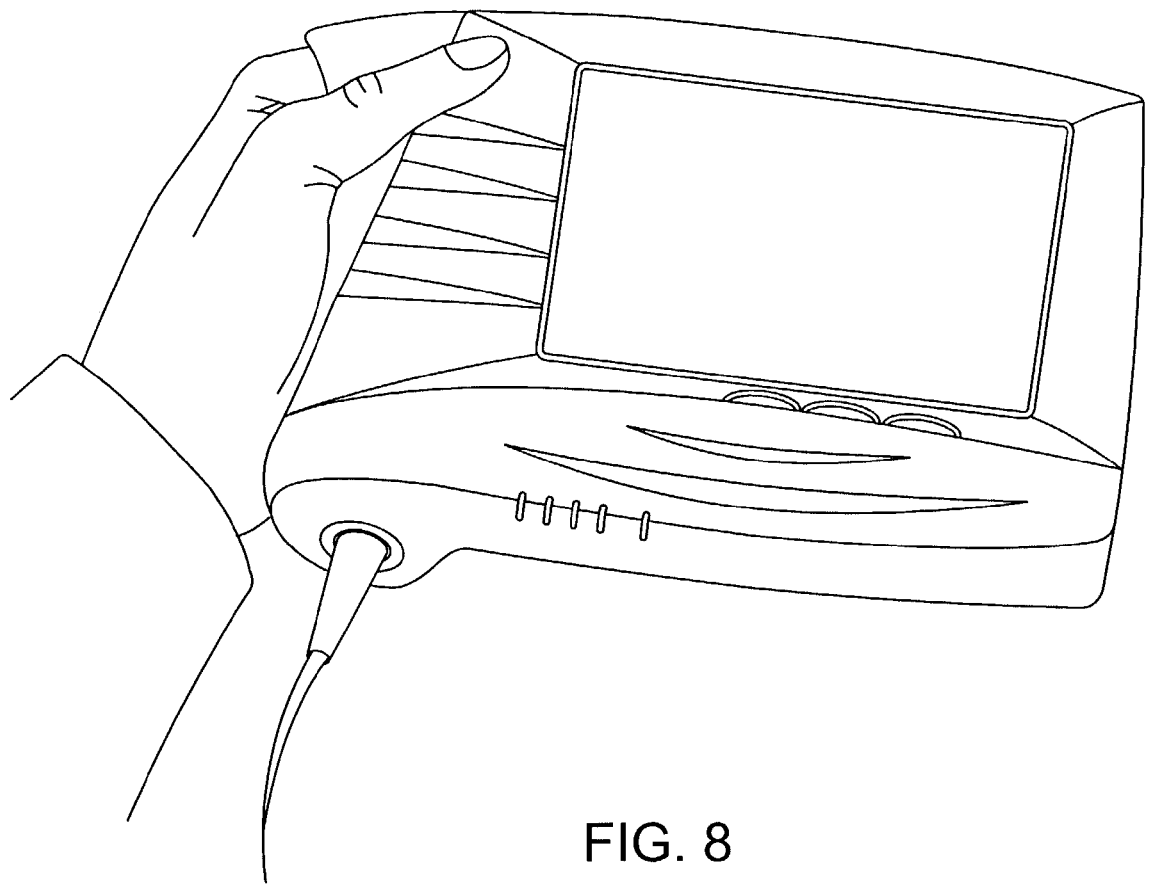
Figure 9:
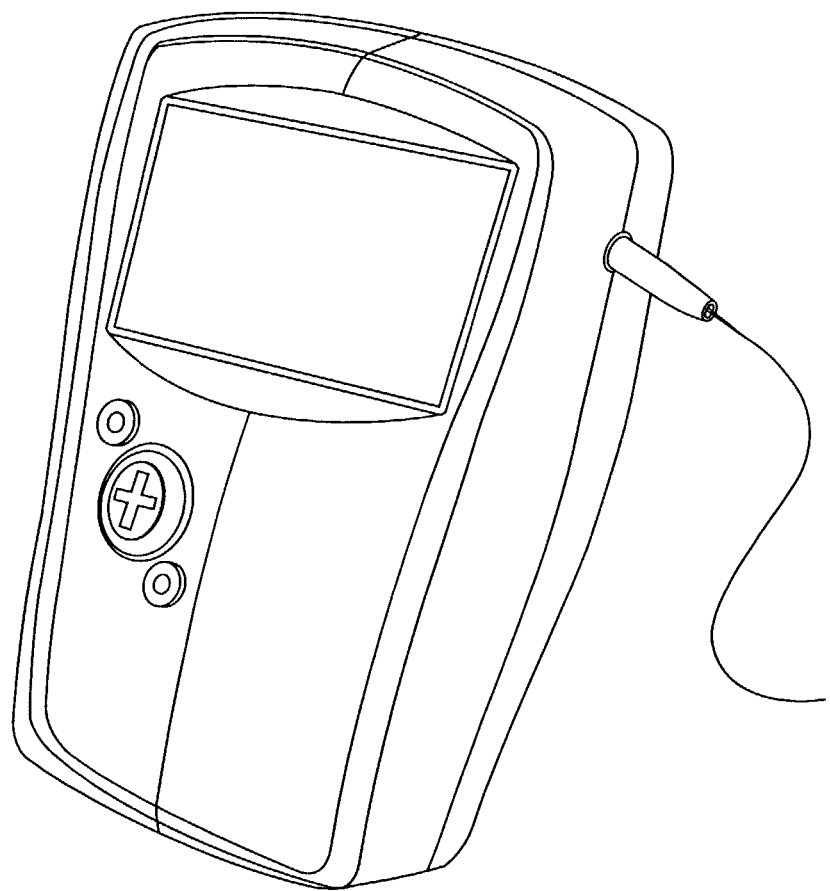
Figure 10:
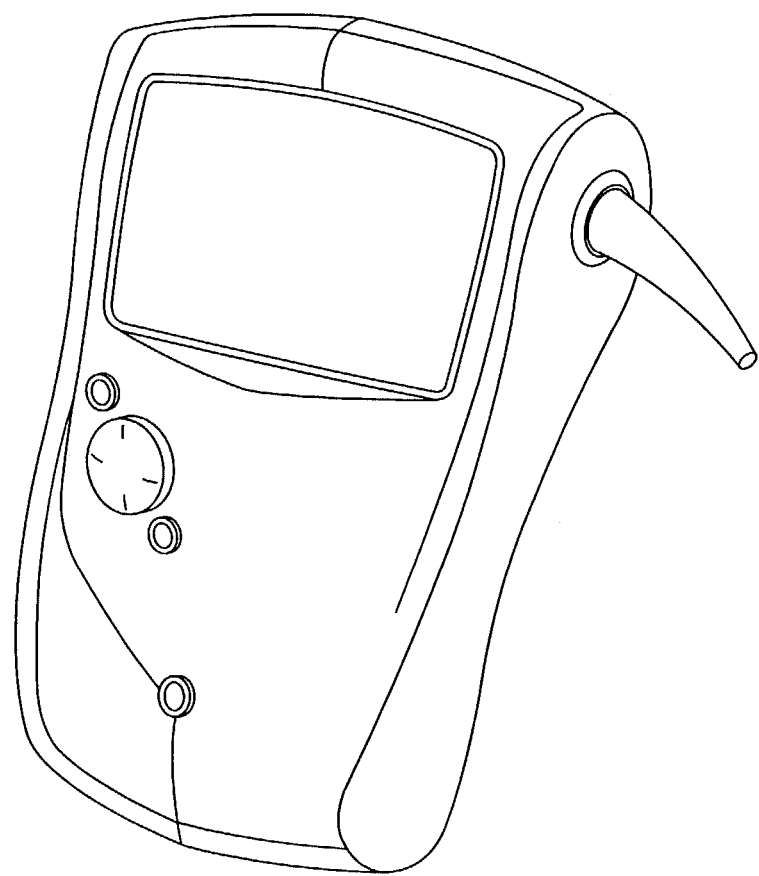
Figure 11:
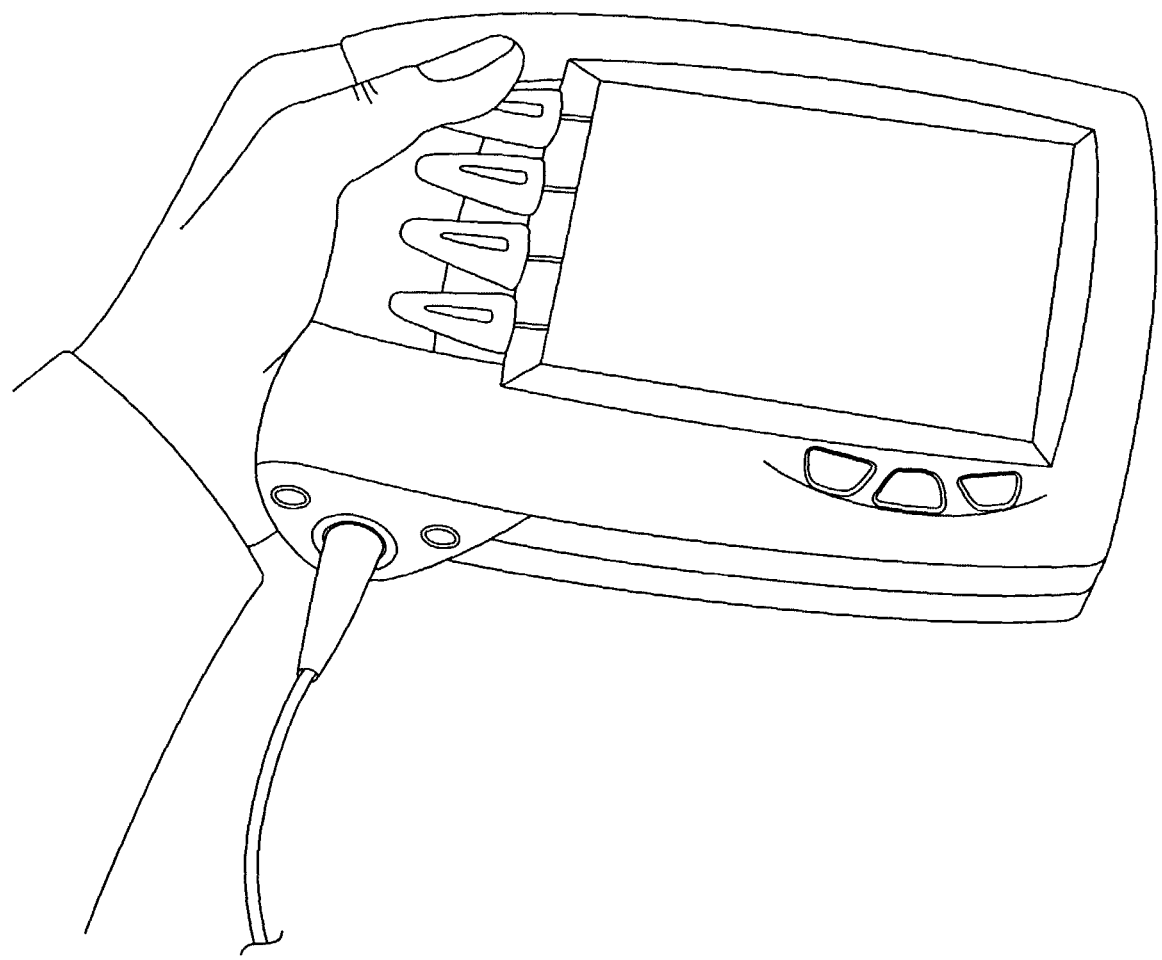
Figure 12:
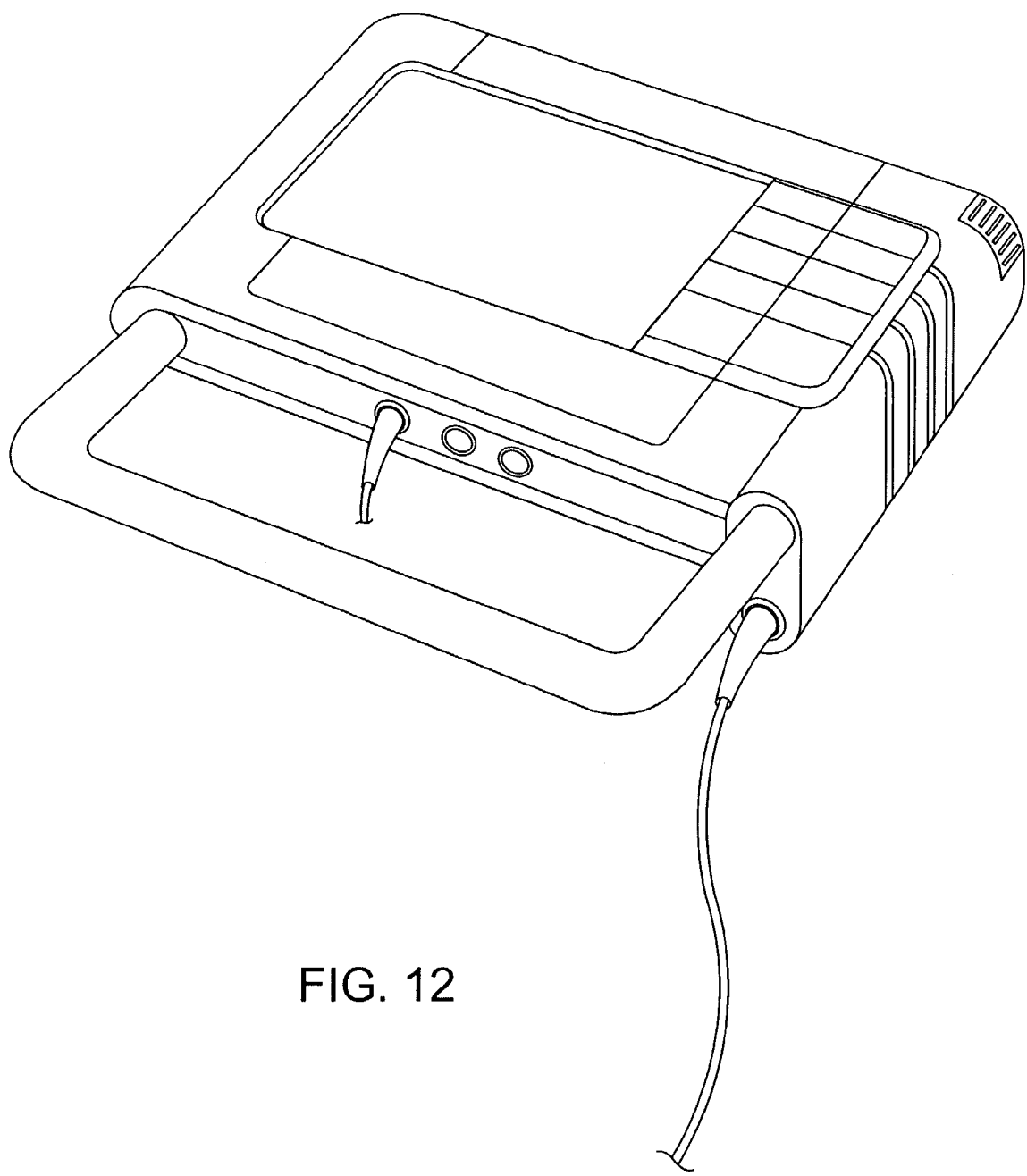
Figure 13:
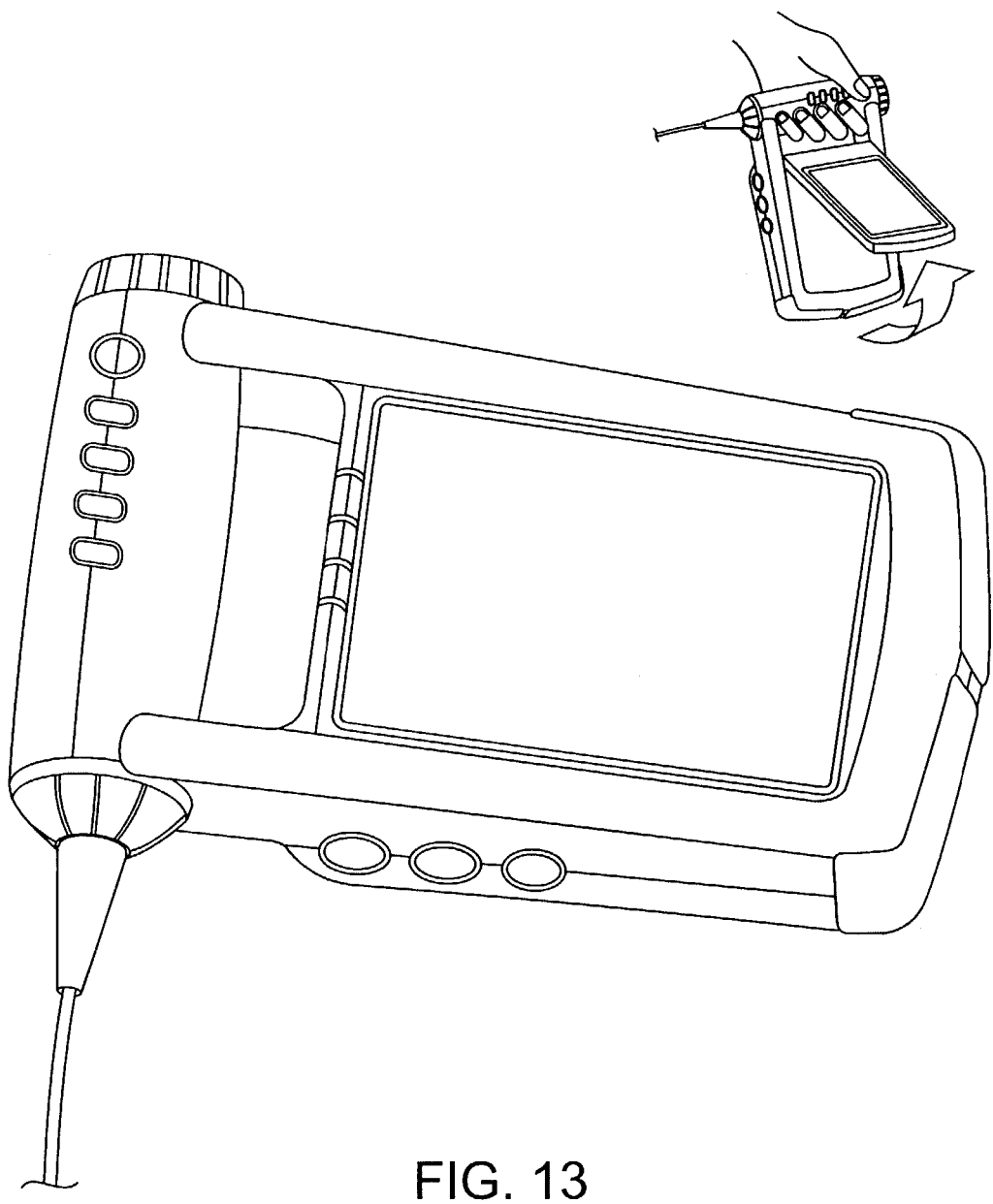
Figure 14:
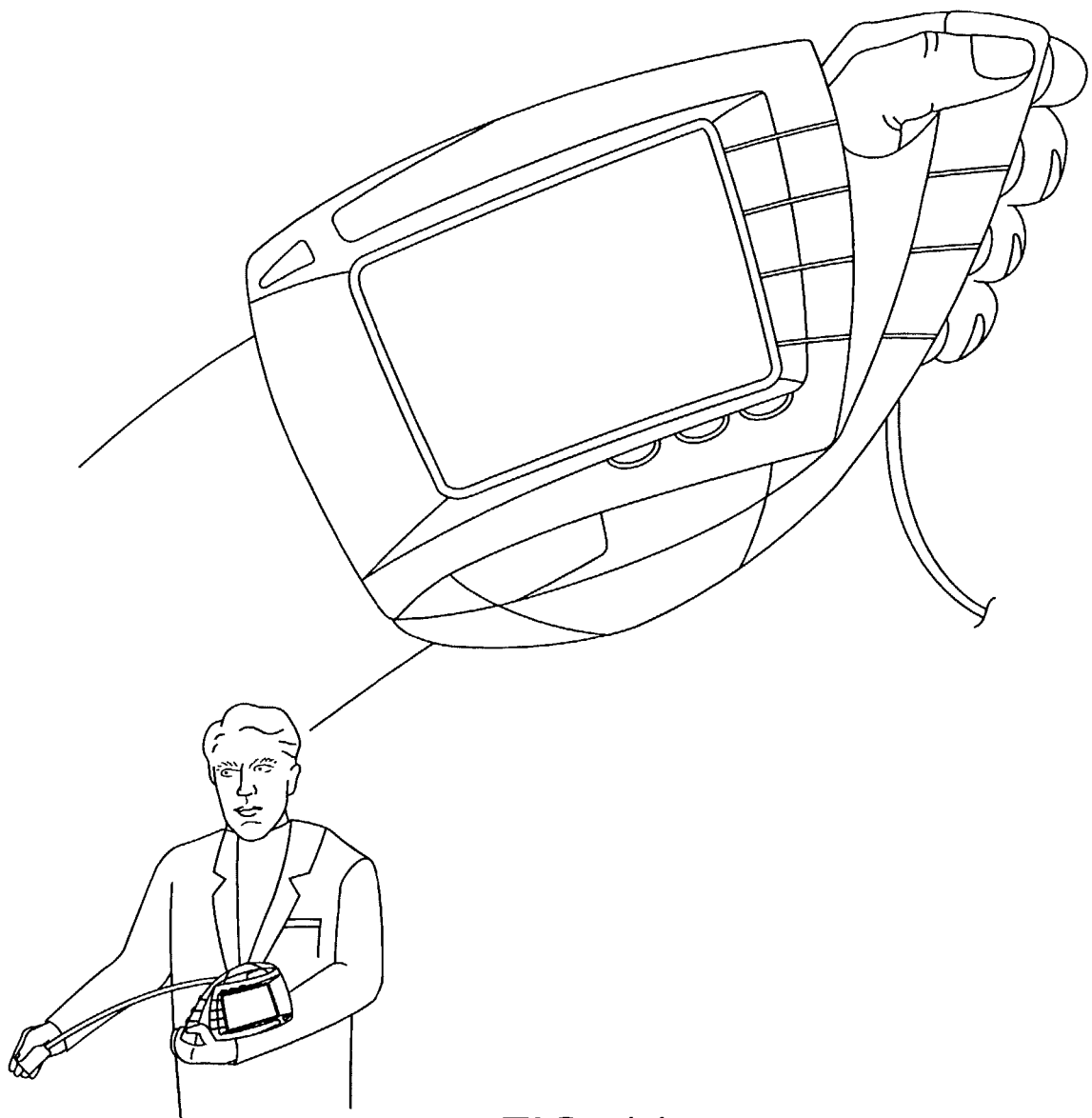
Figure 15:
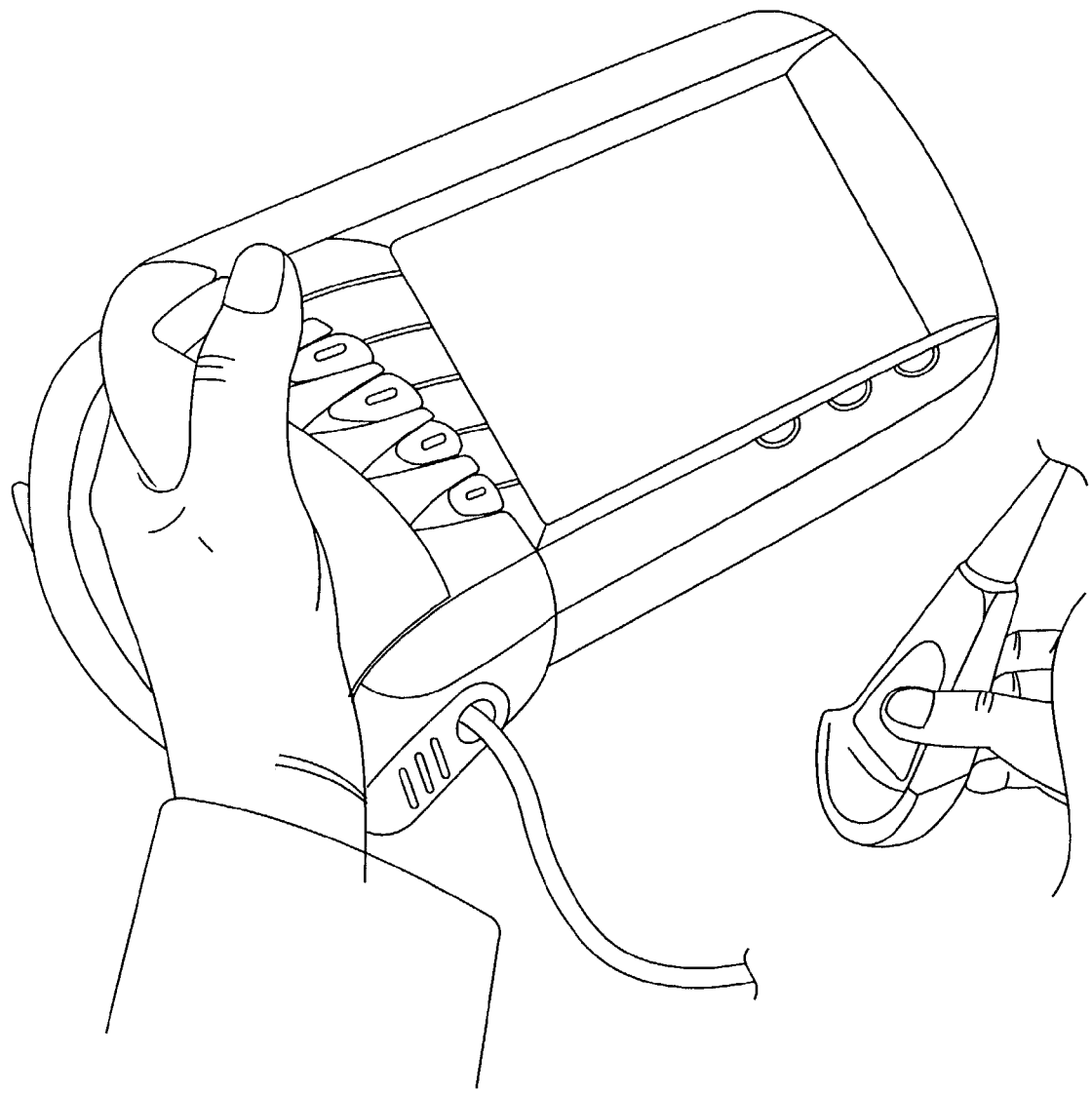
Figure 16:
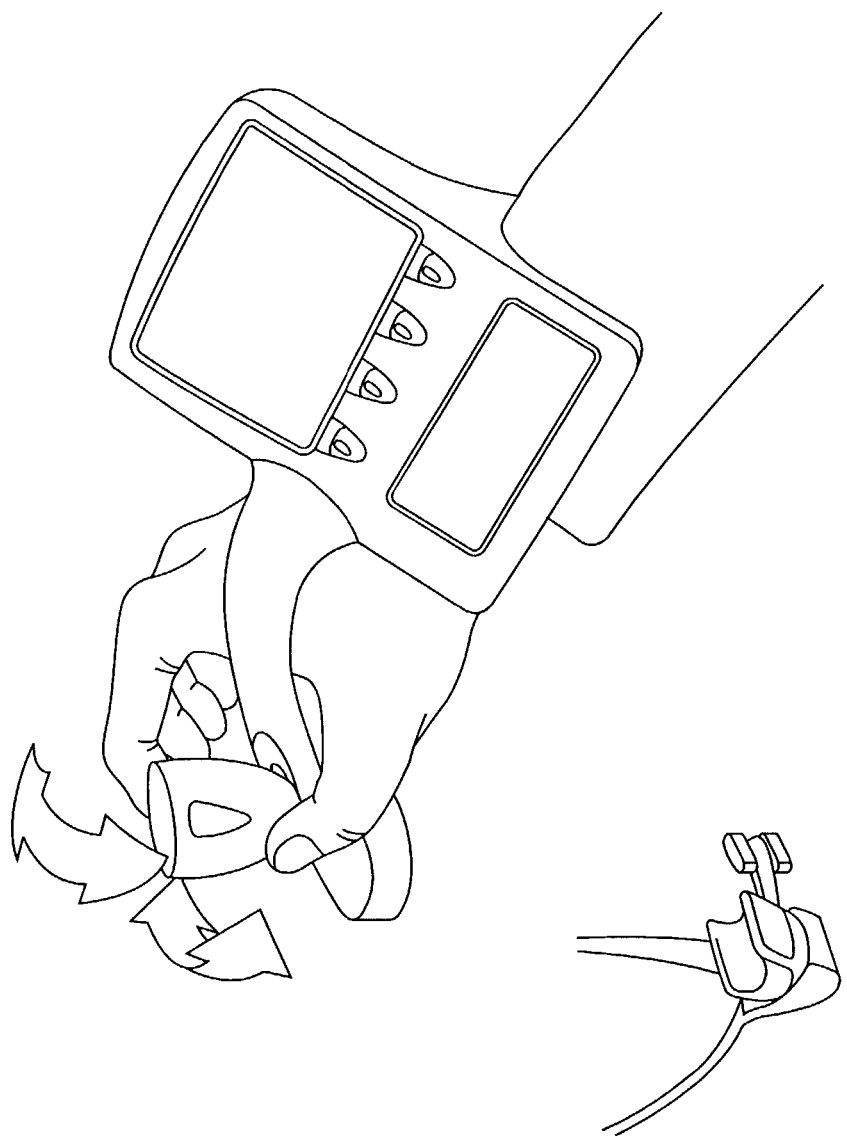
Figure 17:
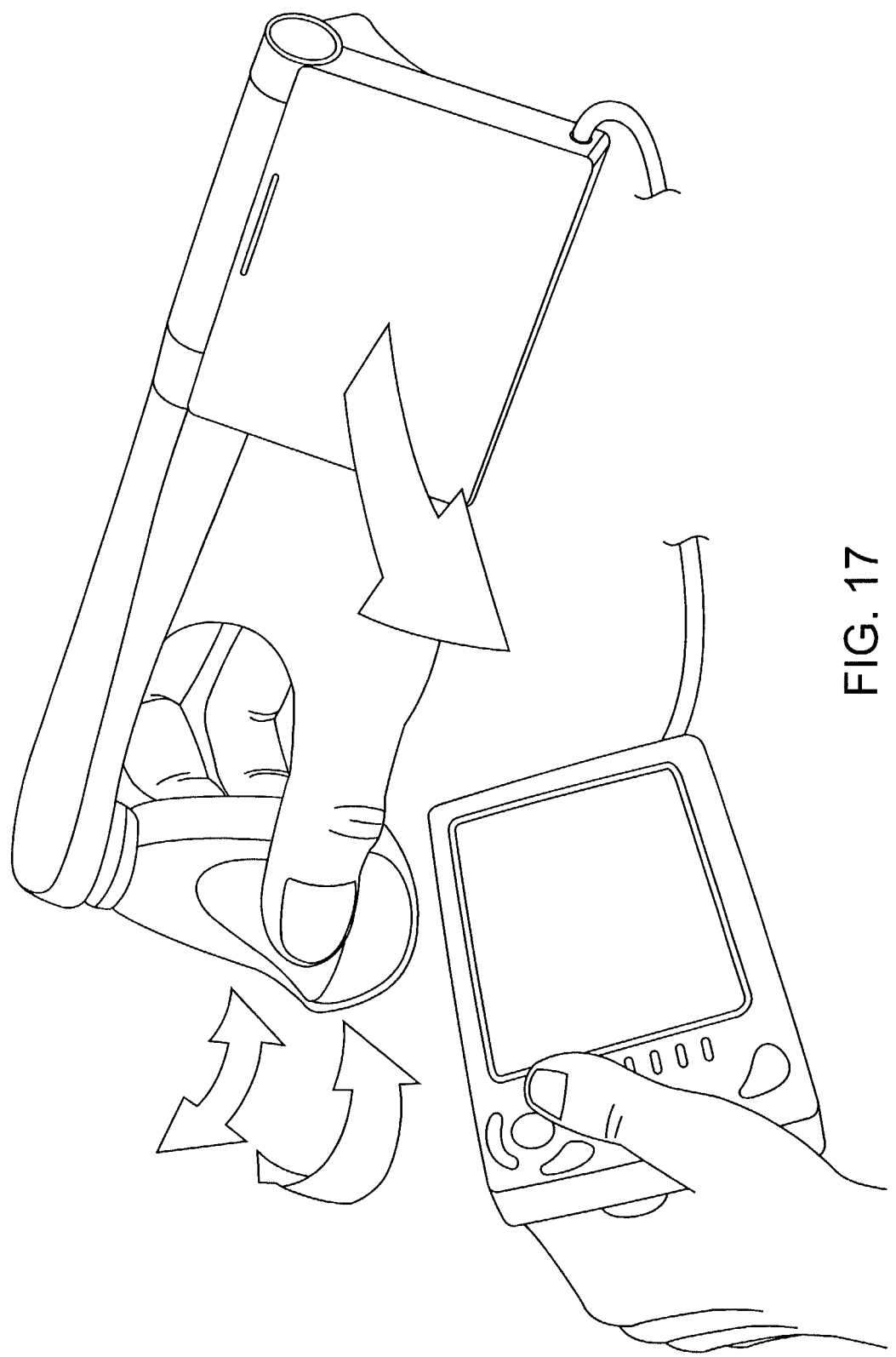
Figure 18:
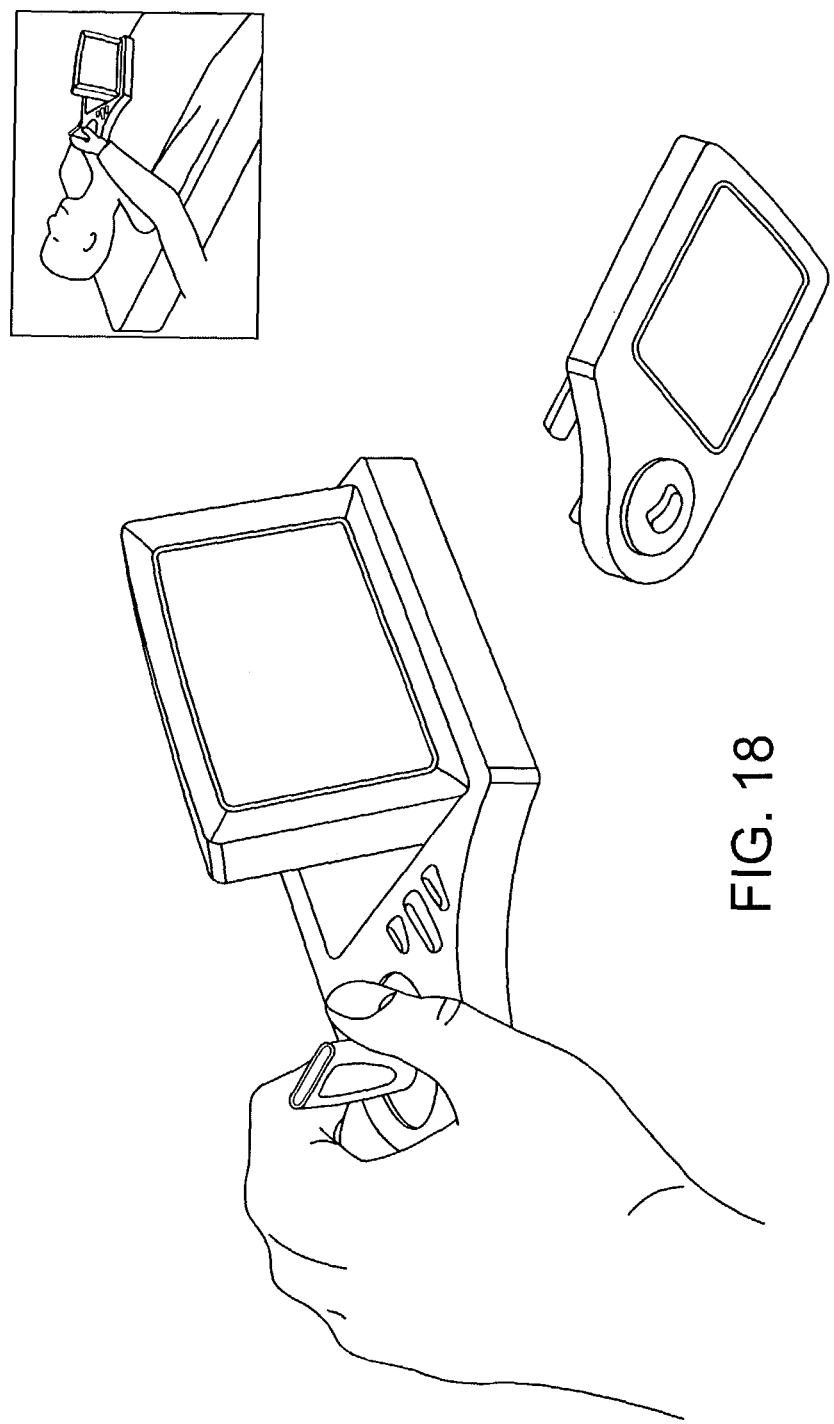
Figure 19:
Figure 20:
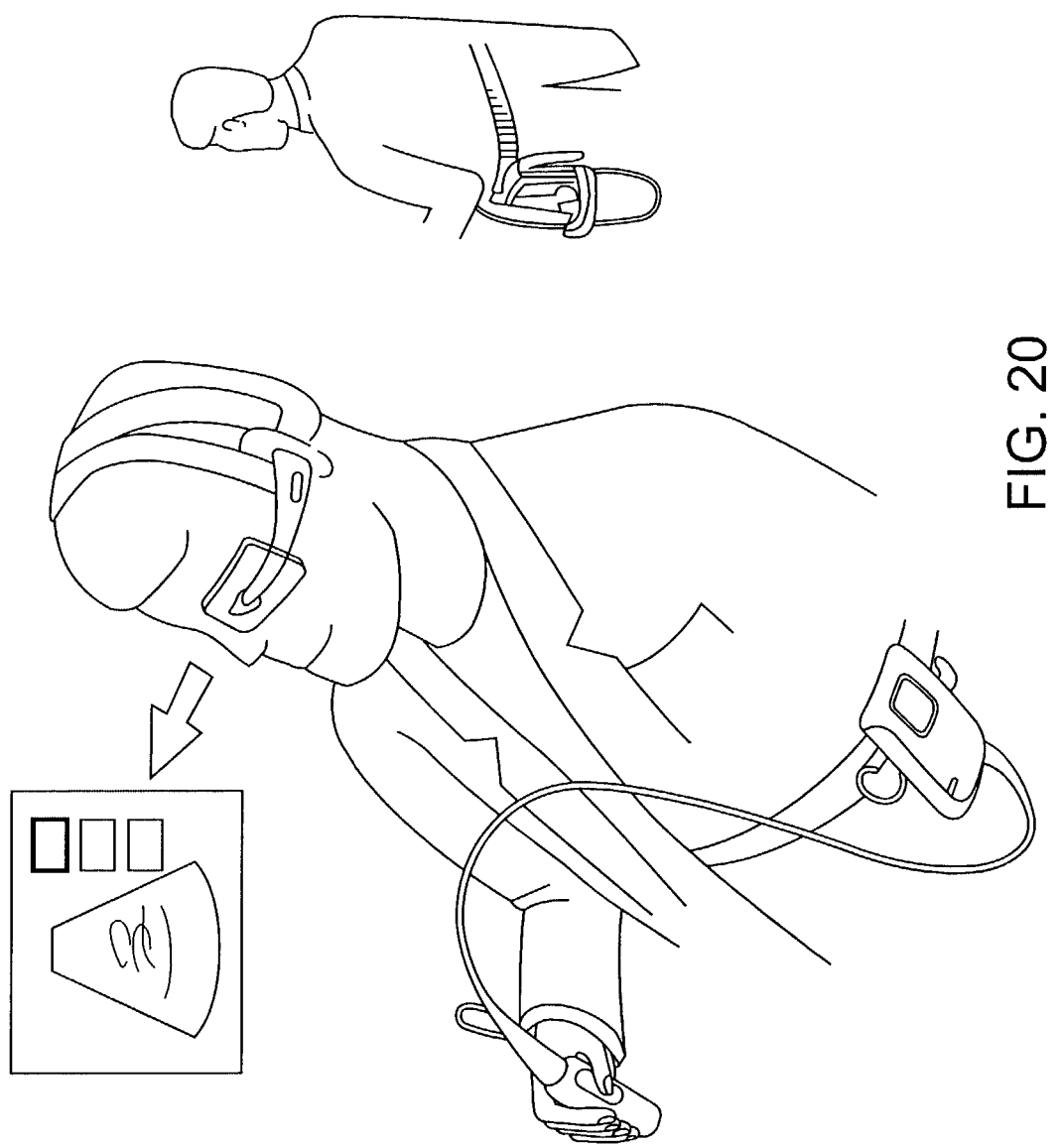

FIG. 1D illustrates a right-handed model of the present invention, where the controls are a mirror image of those in FIGS. 1A-C.

The medical ultrasound system also allows for the entry of a key code to permit upgrades to the software of the device. The operation of the key code is explained in greater detail in co-pending U.S. application Ser. No. 09/840,002, the contents of which are incorporated herein by reference.

A second embodiment of the present invention forms a lightweight ultrasound instrument comprising a body having a power supply, a user interface for controlling the instrument, a display screen, and a system electronics package capable of a plurality of diagnostic ultrasound modes. In this embodiment, the body may optionally be a balance body. A transducer assembly is attached to the body via a wire or thin flexible cable, the transducer assembly comprises a digital beam former, an A/D converter circuit and a transducer array. The body, transducer assembly and wire combined weigh less than three pounds.

The wire connecting the body and transducer assembly provides power to the transducer assembly, and a signal path for the body and transducer assembly to communicate using digital data. In this manner the need for an analog cable, having many data paths for analog signals, is eliminated, and spares additional weight. The signal from the transducer array returns through the digital beam former incorporated into the transducer assembly so only digital information goes between the body and the transducer assembly.

The control elements of the lightweight ultrasound instrument are similar to those described above. A plurality of control elements, of which one is preferably a D-controller, and a touch screen. Again the body can be held with one hand, so the users thumb, or fingers can access the D-controller on the body.

In a third embodiment, a wireless diagnostic ultrasound system comprises a first body, and a second body. The first body is the main unit having system electronics, a user interface having a display screen and at least one control element, a first wireless transmit/receive circuit and a first power supply. The second body is a transducer assembly having a digital beam former, an A/D converter circuit, a transducer array, a second power supply and a second transmit/receive element such that the digital beam former of the second body can be controlled by the system electronics of the first body using the first and second transmit/receive circuits. The first and second transmit/receive circuits being a wireless means for communicating between the first body and the second body. Wireless data transfer and communication are well-understood technologies. Any standard wireless transmission standard capable of supporting the digital information communication of the present invention may be used.

The display screen in this embodiment is preferably a touch screen as well. The use of a touch screen permits the same advantages for ease of use to a user as previously described. A D-controller as one of the control elements allows for simple one-handed operation of the first body while the second hand holds the transducer assembly in place. The wireless design permits a user total freedom from encumbering cable and wire connections to the first body such that the transducer array can be positioned easily for manual steering.

In a fourth embodiment, the invention comprises of a first body having system electronics, a first transmit and receive element, and a first power supply. The first body weighing less than two pounds. A second body houses the transducer assembly. The transducer assembly has a digital beam former, an A/D circuit, a transducer array, a second power supply, a second transmit and receive element and at least one control element. The second body weighing less than one pound. A head set is provided comprising a visual display, a receive element and a third power supply such that the first body, second body and head set are all in real time communication with each other. The user can control the system through the second body or first body while visualizing the ultrasound scan though the head set. Voice recognition capability can be added to the head set through a head set microphone, allowing a user to command the operation of the ultrasound system at some level using voice activated commands instead of one or more of the manual control elements.

What is claimed is:

1. A diagnostic ultrasound system comprising:
a balance body ultrasound unit weighing less than three and a half pounds (3.50 lbs), wherein said balance body ultrasound unit comprises a battery, and wherein balance of said balanced body results from predetermined arrangement of internal components of said balanced body including said battery; and
a docking station having a data I/O bus for communicating with said balance body unit, and a power relay for recharging the battery of said balance body ultrasound unit.

2. The diagnostic ultrasound system as described in claim 1, wherein said docking station further comprises an aperture for receiving and charging a second battery.

3. The diagnostic ultrasound system as described in claim 1 wherein said balance body ultrasound unit's center of gravity is positioned close to the strength of a user's hand.

4. A diagnostic ultrasound system comprising:
a balance body ultrasound unit weighing less than three and a half pounds (3.50 lbs), wherein said balance body ultrasound unit comprises a battery and said balance body ultrasound unit's center of gravity is positioned close to the strength of a user's hand and an aperture is positioned at least partially between said battery and system electronics of said balance body ultrasound unit; and
a station having a data I/O bus for communicating with said balance body unit, and a power relay for recharging the battery of said balance body ultrasound unit.

5. A diagnostic ultrasound system comprising:
a balance body ultrasound unit weighing less than three and a half pounds (3.50 lbs), wherein said balance body ultrasound unit comprises a battery and said balance body ultrasound unit's center of gravity is positioned close to the strength of a user's hand and wherein balance of said balanced body results from predetermined arrangement of said balance body's internal components, including said battery, around an aperture; and
a station having a data I/O bus for communicating with said balance body unit, and a power relay for recharging the battery of said balance body ultrasound unit.

* * * * *